US011766531B2

(12) United States Patent
Baillie et al.

(10) Patent No.: US 11,766,531 B2
(45) Date of Patent: Sep. 26, 2023

(54) FLOW REGULATED, TIME CYCLED HIGH FREQUENCY PERCUSSIVE VENTILATOR

(71) Applicant: Percussionaire Corporation, Sandpoint, ID (US)

(72) Inventors: Mark Baillie, Sandpoint, ID (US); Shawn Goughnour, Sandpoint, ID (US); Giles Wilson, Sandpoint, ID (US)

(73) Assignee: Percussionaire Corporation, Sandpoint, ID (US)

( * ) Notice: Subject to any disclaimer, the term of this patent is extended or adjusted under 35 U.S.C. 154(b) by 344 days.

(21) Appl. No.: 17/210,855

(22) Filed: Mar. 24, 2021

(65) Prior Publication Data
US 2021/0299374 A1  Sep. 30, 2021

Related U.S. Application Data

(60) Provisional application No. 63/000,515, filed on Mar. 27, 2020.

(51) Int. Cl.
*A61M 16/00* (2006.01)
*A61M 16/08* (2006.01)
(Continued)

(52) U.S. Cl.
CPC .......... *A61M 16/022* (2017.08); *A61M 11/06* (2013.01); *A61M 16/0006* (2014.02);
(Continued)

(58) Field of Classification Search
CPC .............. A61M 16/00; A61M 16/0006; A61M 16/0057; A61M 16/0096; A61M 16/022;
(Continued)

(56) References Cited

U.S. PATENT DOCUMENTS

| | | | |
|---|---|---|---|
| 5,165,398 A | | 11/1992 | Bird |
| 5,862,802 A | * | 1/1999 | Bird .................... A61M 16/021 |
| | | | 128/204.21 |

(Continued)

FOREIGN PATENT DOCUMENTS

| | | |
|---|---|---|
| WO | 02/43643 A2 | 6/2002 |
| WO | 2016057847 A1 | 4/2016 |

OTHER PUBLICATIONS

IPV®-1C ventilator product information page retrieved from https://web.archive.org/web/20190313150804/https://percussionaire.com/products/ipv-1c with date Mar. 13, 2019.*

(Continued)

*Primary Examiner* — Joseph D. Boecker
(74) *Attorney, Agent, or Firm* — Finch & Maloney PLLC

(57) ABSTRACT

The control-monitor, used in combination with a percussive ventilation breathing head and internal reciprocating injector shuttle, includes in a casing a generator, sensory pulse amplitude, frequency and MAP modules and a gas amplitude and pulsatile frequency control knobs. First and second AMP control indicia include a bent conical AMP indicia (a wide span indicating greater amplitude, a narrow span indicating lesser amplitude) and a single waveform with an adjacent double-headed arrow vertical line. First and second F control indicia include a bent conical F indicia (a wide span indicating greater F and a narrow span indicating lesser F) and multiple waveforms with an adjacent double-headed arrow horizontal line.

7 Claims, 8 Drawing Sheets

(51) Int. Cl.
*A61M 16/12* (2006.01)
*A61M 11/06* (2006.01)
*A61M 16/20* (2006.01)

(52) U.S. Cl.
CPC .... *A61M 16/0096* (2013.01); *A61M 16/0858* (2014.02); *A61M 16/127* (2014.02); *A61M 16/20* (2013.01); *A61M 2016/0027* (2013.01); *A61M 2205/502* (2013.01); *A61M 2205/584* (2013.01); *A61M 2209/08* (2013.01)

(58) Field of Classification Search
CPC ............ A61M 16/0858; A61M 16/127; A61M 16/20; A61M 2205/502; A61M 11/00; A61M 11/06
See application file for complete search history.

(56) References Cited

U.S. PATENT DOCUMENTS

| | | | |
|---|---|---|---|
| 6,581,600 | B2 | 6/2003 | Bird |
| 6,595,203 | B1 | 7/2003 | Bird |
| 8,347,883 | B2 | 1/2013 | Bird |
| 2003/0010344 | A1* | 1/2003 | Bird ...................... A61M 16/12 128/205.24 |
| 2004/0069304 | A1* | 4/2004 | Jam .................... A61M 16/0006 128/204.23 |
| 2009/0126734 | A1 | 5/2009 | Dunsmore et al. |
| 2011/0100360 | A1* | 5/2011 | Faram ................. A61M 16/127 128/202.16 |
| 2014/0163440 | A1* | 6/2014 | Toh .................... A61M 16/0006 601/96 |
| 2014/0190481 | A1* | 7/2014 | Jam ...................... A61M 16/024 128/205.24 |
| 2018/0085541 | A1* | 3/2018 | Ye ...................... A61M 16/0006 |
| 2020/0139076 | A1 | 5/2020 | Baillie et al. |

OTHER PUBLICATIONS

IPV®-2C ventilator product information page retrieved from https://web.archive.org/web/20190312224759/https://percussionaire.com/products/ipv-2c with date Mar. 12, 2019.*

VDR®-4 ventilator product information page retrieved from https://web.archive.org/web/20190313225723/https://percussionaire.com/products/vdr-4 with date Mar. 13, 2019.*

* cited by examiner

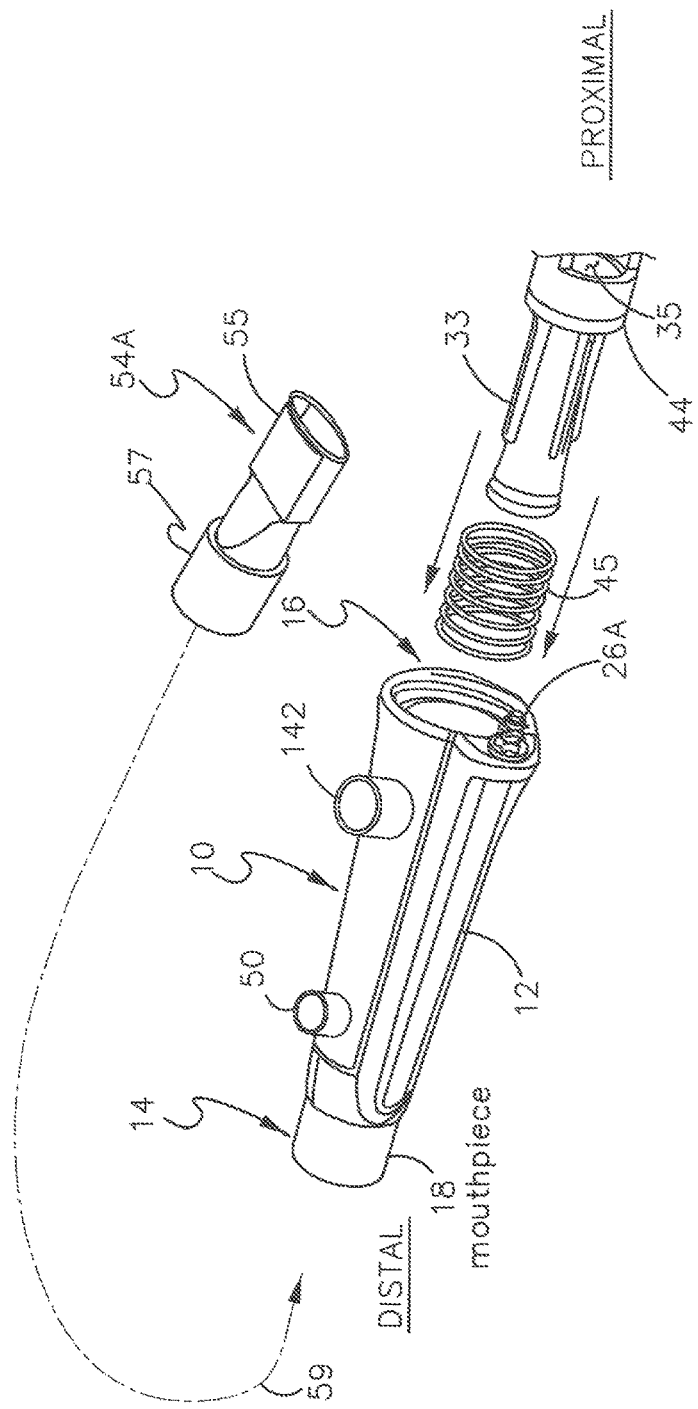

FLOW REGULATED, TIME CYCLED HIGH FREQUENCY PERCUSSIVE VENTILATOR

This is a non-provisional patent application based upon and claiming the benefit of provisional patent application Ser. No. 63/000,515, filed Mar. 27, 2020, the contents of which is incorporated herein by reference thereto. The present invention relates to a flow regulated, time cycled high frequency percussive ventilator specially designed to be simple to connect and operate by nominally trained medical technicians. The flow regulated, time cycled high frequency percussive (FRTC) ventilator is controlled by a control system which enables the supply of a flow of pulsatile gas and which monitors pressure in the FRTC breathing head via a pressure sensor line, this pressure indicating the condition of the patient. The contents of U.S. patent application Ser. No. 16/391,481, filed Apr. 23, 2019, published U.S. Patent Publication 20200139076, is incorporated herein by reference thereto.

BACKGROUND OF THE INVENTION

Certain percussive ventilation breathing heads have been disclosed in prior patents. One configuration of a percussive ventilation breathing head is described in U.S. Pat. No. 6,595,203 to Bird, the contents of which is incorporated herein by reference thereto.

The frequency regulated, flow interrupted (FRTC) ventilator has a breathing head which administers intermittent percussive ventilation to a patient's airway. Prior art percussive ventilator systems generally were designed for use by trained medical professionals. As such, the operator interfaces were cluttered with knobs, buttons, analog displays showing current and dynamic operational data, and several hoses (one for delivery of percussive gas pulses, and another as pressure sensing monitor hose).

The inventive FRTC ventilator includes several improvements, such as color-coded lines and couplers enabling nominally trained medical professionals to quickly attach the correct line from the control-monitor to the FRTC breathing head, control dial or knob indicia on the control-monitor graphically presenting information informing such that nominally trained professionals can control the use of the FRTC, and a highly simplified display screen. Further improvements provide for a FRTC breathing head which is simple to clean or dispose after multiple use.

The need for a compact, simple to use FRTC ventilator enables rapid deployment during epidemics and quick, on the job training for the casual user. The casual user, once trained, is identified herein as a nominally trained medical professional. Since the compact, simple to use FRTC ventilator is highly portable, such nominally trained medical professional typically needs no further training once the FRTC is moved patient-to-patient since decoupling, hook-up, initial patient control settings and during-use patient monitoring is readily apparent by the inventive simplified control and monitoring interface.

OBJECTS OF THE INVENTION

It is an object of the present invention to provide a simplified FRTC ventilator with a percussive ventilation breathing head. This new breathing head which is simple to clean or dispose after multiple use.

It is another object of the present invention to provide a simple control interface for the control-monitor unit deployed as a FRTC ventilator. The simple controller interface has specially configured indicia for nominally trained professionals. The controller displays, showing in-use operational conditions and status, are also simplified for nominally trained professionals.

It is a further object of the present invention to provide extremely easy connectivity between the FRTC ventilator breathing head and the FRTC configured control-monitor.

Another advantage of the present invention is that, once the FRTC is moved from one patient to another, hook-up, initial patient control settings and during-use patient monitoring is readily apparent by the inventive simplified control and monitoring interface.

SUMMARY

The flow regulated, time cycled (FRTC) ventilator is controlled by a control system which supplies the FRTC ventilator breathing head with a flow of pulsatile gas and which monitors pressure in the breathing head via a pressure sensor line, this pressure indicating the condition of the patient. The contents of U.S. patent application Ser. No. 16/391,481, filed Apr. 23, 2019 is incorporated herein by reference thereto.

The FRTC ventilator has a breathing head which administers intermittent percussive ventilation to a patient's airway. The inventive FRTC ventilator includes several improvements, such as color-coded lines and couplers enabling nominally trained medical professionals to quickly attach the correct line from the control-monitor to the breathing head, indicia on the control-monitor graphically presenting information informing to the nominally trained professional as to the use of the FRTC and a simple operational in-use display screen. Also, the breathing head is simplified for cleaning or disposal.

The percussive ventilation breathing head is adapted to be supplied with a flow of pulsatile gas fed to an elongated breathing head body at a proximal end thereof. The gas is supplied by a control-monitor. As used herein, "proximal" refers to the end of the breathing head body where the gas is supplied. The term "distal" is opposite the proximal end. The patient inhales and exhales medicated or non-medicated aerosol gas at the distal end of the breathing head body directly or through an intermediate tube.

The breathing head body defines an interior passageway therein. A reciprocating injector shuttle is movably mounted in the breathing head passageway. The shuttle moves distally due to the pulsatile gas, assisted by a diaphragm and a venturi-like jet nozzle. In some configurations, the nozzle pulls nebulized aerosol from a depending plenum and a nebulizer attached below the depending plenum. U.S. patent application '481 shows and describes the nebulizer action and depending plenum.

The shuttle is biased in a proximal direction within the interior passageway and moves proximally due to the bias. The shuttle defines an internal flow passage from a proximal shuttle input port to a distal shuttle output port at the distalmost mouth of the percussive ventilation breathing head body. The patient is fluidly connected to the distalmost mouth.

The FRTC ventilator has a breathing head with an entrainment valve port in fluid communication ("fluid" refers to air flow or aerosol flow) with the proximal shuttle input port. The entrainment valve is fluidly connected to the ambient environment. When the pressure in the internal shuttle flow passage falls below a predetermined value (set by the entrainment valve port), the valve port opens to the ambient and ambient air is introduced into the proximal shuttle input port area. The entrainment valve is also adapted to release pressure to the ambient at a different predetermined pressure. Details of the entrainment port are found in U.S. patent application '481.

The elongated breathing head body also includes an end cap having, on a proximal cap region, a color-coded aerosol tube fitting adapted to receive the pulsatile gas flow thereat. The color-coded fitting matches the color coding on the pulsatile gas supply tube coupled, at one end to the breathing head aerosol tube fitting and, at the other end, to the control-monitor, which also has a similar color-coded fitting for the gas supply tube. The breathing head end cap has, on a distal cap region, the diaphragm mounted thereon. The diaphragm forms an expandable chamber between the diaphragm and the distal cap region. Pulsatile gas flow from the aerosol tube fitting expands the diaphragm's expandable chamber. The venturi-like jet nozzle is mounted on the diaphragm at a distal diaphragm region. The venturi-like jet nozzle is in fluid communication with the expandable chamber and the proximal shuttle input port, thereby permitting pulsatile gas flow to the proximal shuttle input port. The shuttle moves distally due to the diaphragm movement and the pulsatile gas ejected from the venturi-like jet nozzle into the proximal shuttle input port. The shuttle is biased in a proximal direction within the breathing head passageway by a biasing means and moves proximally due to the biasing means.

The percussive ventilation breathing head has (a) an operational configuration wherein upon application of the pulsatile gas, the shuttle is adapted to move distally into the shuttle passageway and then move proximally due to a biasing spring or other biasing mechanism, and (b) a disassembled cleaning mode wherein the end cap is removed from the proximal end of the elongated breathing head body and the shuttle is withdrawn from the breathing head body interior passageway, such that the end cap, elongated breathing head body, and shuttle is adapted to be cleaned. The spring is removed for cleaning.

To connect the percussive ventilation breathing head to a control system (the control system also supplying pulsatile gas and pressurized gas to the breathing head), the pressure supply end of the gas pressure tube and the pulsatile supply end of the pulsatile gas tube terminates in a color-coded fitting which color coding matches the color coding on the fitting on the control-monitor.

BRIEF DESCRIPTION OF THE DRAWINGS

Further objects and advantages of the present invention can be found in the detailed description of the embodiments when taken in conjunction with the accompanying drawings.

FIG. 1B shows the control-monitor on the I.V. stand and FIG. 1C shows the simple claim on the stand.

FIG. 4 diagrammatically illustrates the FRTC ventilator breathing head partly disassembled.

DETAILED DESCRIPTION OF EMBODIMENTS OF THE INVENTION

The FRTC ventilator breathing head administers intermittent percussive ventilation to a patient's airway. During an inhalation phase, the patient pulls ambient gas into his or her lungs through the percussive ventilation breathing head. During pulsatile gas flow, additional gas pulses are provided to the patient during inhalation. During exhalation, pressure sensitive systems in the FRTC ventilator percussive breathing head permit exhalation through an exhalation port to fluidly connect tube (not shown) in the breathing head.

Figure 1A:
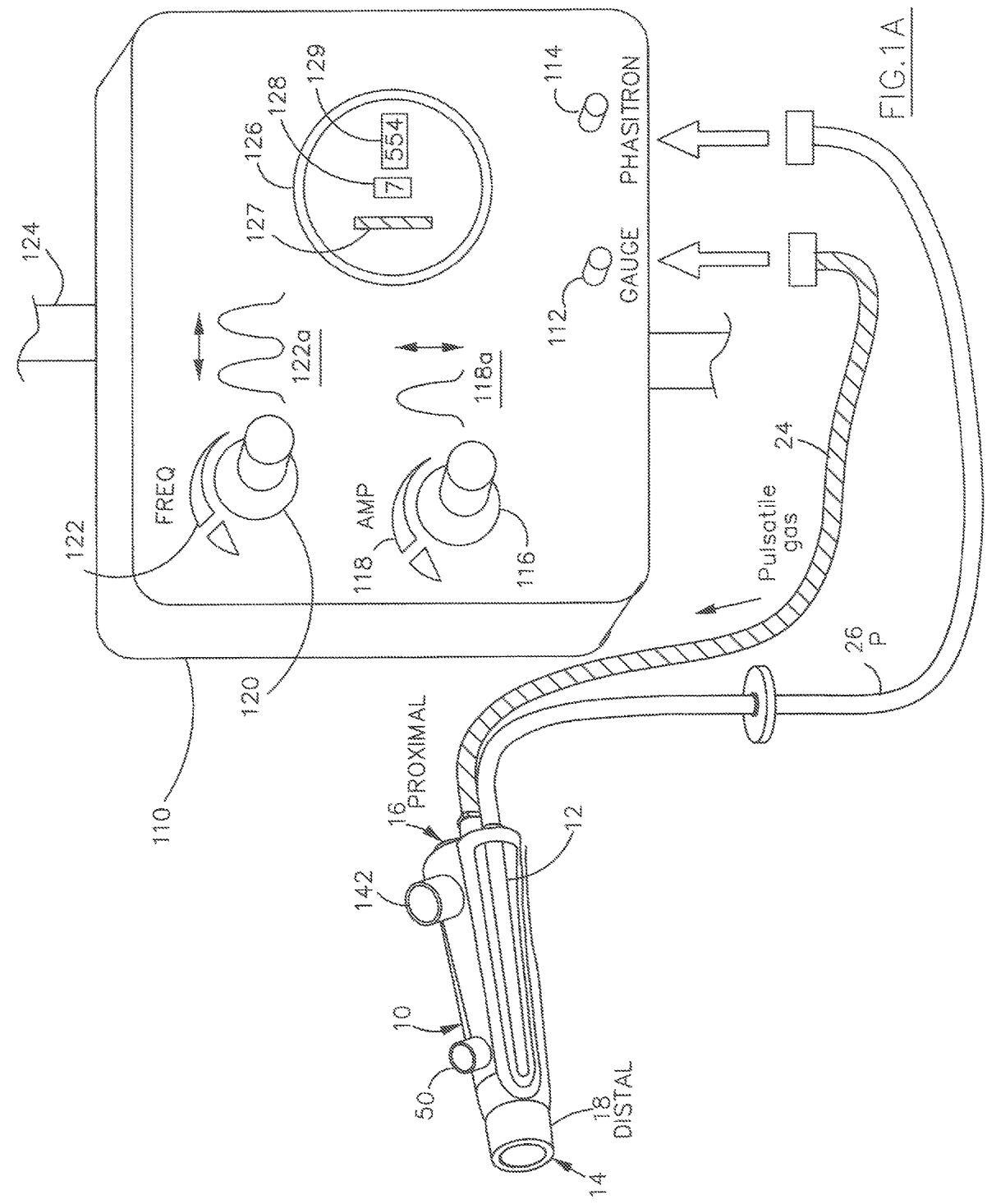
FIGS. 1A, 1B and 1C show the system wherein FIG. 1A diagrammatically illustrates the FRTC ventilator breathing head pneumatically coupled to a control-monitor 110. The breathing head includes a distal end 14, defined by a mouthpiece, and a proximal end 16 which is supplied with pulsatile gas.
Figure 2A:
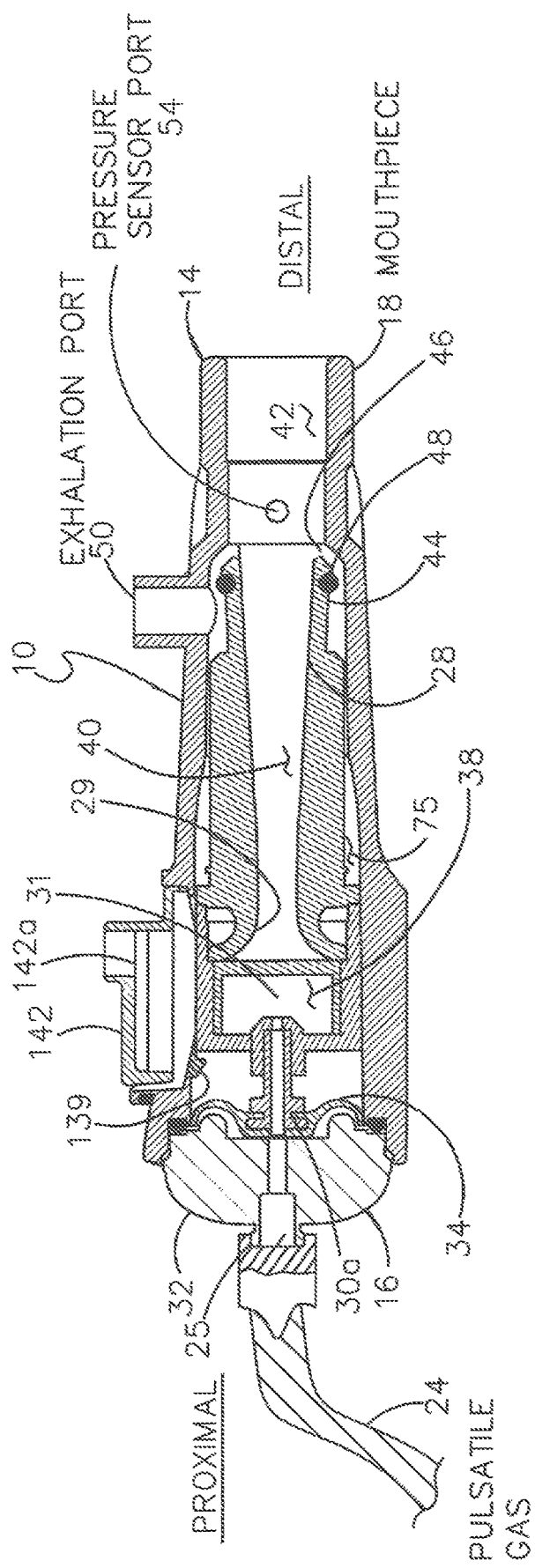
FIG. 2A diagrammatically illustrates a cross-sectional view of the FRTC ventilator breathing head.

FIG. 1A diagrammatically illustrates breathing head 10 generally pneumatically coupled to gas supply and control apparatus 110. This control-monitor 110 includes a casing with a control-display face including control knobs 118, 120 and operational display 126. Breathing head 10 includes a distal end 14 defined by patient-side mouthpiece 18 and a supply-side proximal end 16. Exhalation port 50 is shown in FIGS. 1A and 2A. Breathing head 10 includes a side view passage 12 (a transparent tube body) which fluidly couples the distal mouthpiece cavity to the pressure sensor system in the control-monitor 110. Color-coded pulsatile gas supply line 24 is connected to a color-coded end cap at the proximal end 16 of breathing head 10. Pressure (P) sensor tube 26 (differentially color-coded), is coupled at one end to a color-coded gas sensor port 53 (FIG. 2A) on the breathing head 10 and is coupled to the matching color-coded fitting on gas supply and control apparatus 110. Tube 26 permits measurement of gas pressure P in the breathing head and hence the gas pressure supplied to the patient using the breathing head.

Figure 1B:
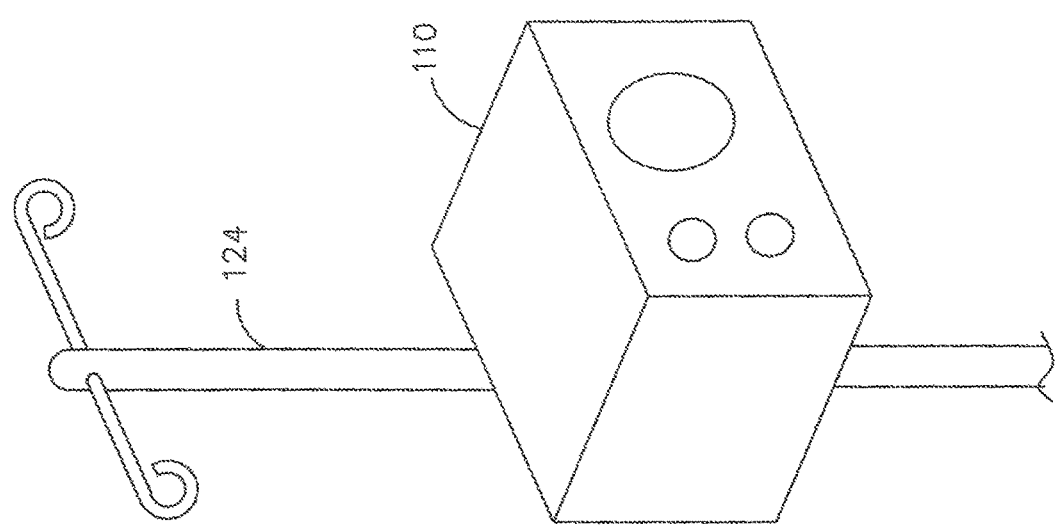
Figure 1C:
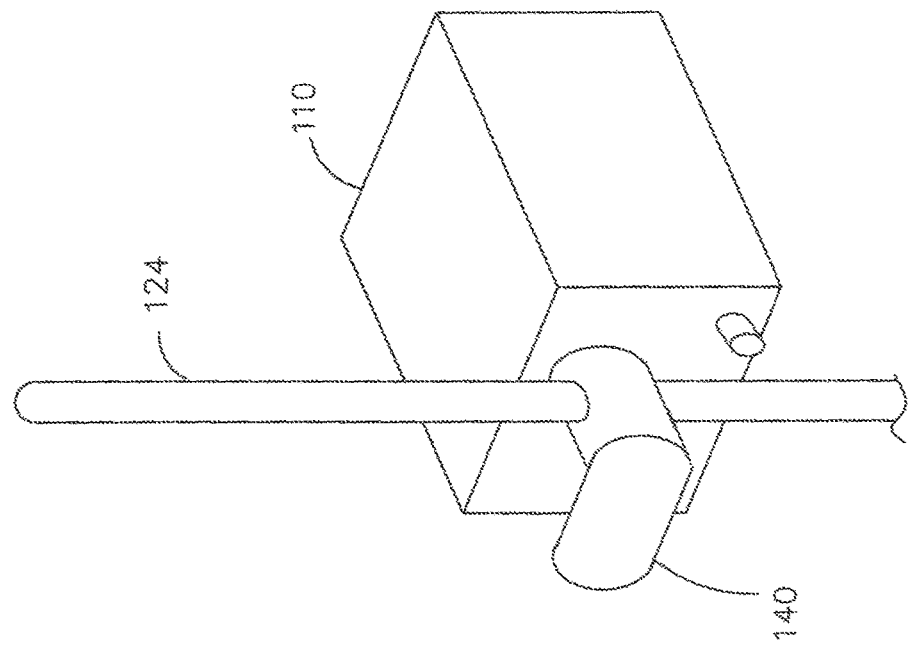

FIG. 1B diagrammatically illustrates control-monitor 110 movably mounted on an I.V. stand 124. FIG. 1C shows that a simple clamp 140 holds the control-monitor 110 on stand 124. The control-monitor 110 weighs slightly more than 1 pound.

The control-monitor 110 (FIG. 1A) has a simple control-monitor interface which includes color-coded gas supply and gas sensor fittings 114, 112 which color matches tubes or lines 26, 24; a display interface 126 with bar graph indicator 127 for pulse amplitude, a mean airway pressure (MAP) numeric display 128 (shown by the number "7"), and a numeric pulse frequency rate indicator 129 (shown by the number "554").

Control knob 116 controls the amplitude (AMP) of the pressurized gas supplied to the patient via the FRTC ventilator breathing head. Importantly, adjacent control graphics 118, 118a show the untrained user of the FRTC what control function is associated with amplitude control knob 116. The control graphic bent conical indicia 118 shows the nominally trained person that a left-turned knob action increases the pulse amplitude. The left turn/increase is graphically presented by the upper arrowhead in control graphic 118a. The bent conical indicia control graphic 188 has a wider conical span on its left-side (also terminating in a separate graphic arrowhead) which further acts as an "increase pulse amplitude" control graphic to visually instruct the nominally trained user. The left-side wider conical span is in contrast to the right-side bent conical span in this control graphic indicia.

This first AMP control indicia (the second being the waveform), above the AMP control knob 116, is defined by with the bent conical indicia 118 with a wide conical span (left-side), indicating application of a greater gas amplitude with complementary counterclockwise rotation of the AMP control knob, compared with the right-side narrow conical span, indicating application of a lesser gas amplitude with complementary clockwise rotation of the AMP control knob. Also, an adjacent AMP control graphic 118a shows a single pulse-wave indicia next to a vertical, double-headed arrow line. The single pulse indicia shows an untrained user that the height (the vertical expanse) the single pulse wave amplitude AMP can be controlled by control knob 116. The second AMP indicia 118a being laterally displaced adjacent the AMP control knob 116 is defined by a vertical single waveform 118a and an adjacent vertical line and up and down arrows. The up arrow indicating application of the greater gas amplitude with the complementary rotation of the AMP control knob (in this embodiment counterclockwise rotation, an ascending knob control), compared with the down arrow indicating application of the lesser gas amplitude with the complementary counter-rotation of the AMP control knob (in this embodiment clockwise rotation). With both control graphics 118, 118a, the untrained user can easily grasp that to lower the amplitude of the gas pulses, follow the lower arrowhead of vertical graphic control 118a, and turn knob 116 clockwise, which clockwise motion is further graphically confirmed by the narrower, right-side illustrated aspect of the bent conical indicia (compared to the wider, left-side of indicia 118). Of course, if the AMP control knob 116 operates to increase the amplitude of the pulsatile gas with clockwise rotation (ascending AMP control operation by right-hand turns), then the control graphic 118 would be a mirror image of the illustrated control graphic. As for control graphic 118b, the double-headed arrow would be on the left-side of the knob 116 to show increasing amplitude gas by clockwise rotation of the knob.

Control knob 120 controls the frequency (Freq or F) of the pressurized gas supplied to the patient via the FRTC ventilator breathing head, and importantly two control graphics are used to illustrate what is the control function of knob 120. The first control graphic is as a bent conical indicia 122 which shows the nominally trained person that a left turn knob movement (counterclockwise) of knob 120 increases the frequency of the pulses. The wider span conical end or left-side end of Freq control graphic 122 illustrates that higher frequency gas pulses are delivered to the patient with a left turn of the knob. The adjacent wave control graphic 122a consists of a multiple pulse wave indicia with a laterally disposed, double headed arrow positioned immediately above the multiple pulse wave indicia. This control graphic also shows the untrained user that frequency of the pulses is controlled by knob 120.

The first and second frequency (F) control indicia (the first being the bent-conical and the second being the multi-waveform indicia) are adjacent to the frequency knob 120. The first F indicia 120a above the F control knob 120 is defined by a bent conical F indicia with a wide conical F span, indicating application of a greater or higher frequency of pulsatile gas with complementary rotation of the F control knob (counterclockwise in the illustrated embodiment). The narrow conical F span of F control indicia 120a indicates application of a lesser or lower frequency of pulsatile gas with complementary counter-rotation of the F control knob 120 (clockwise in this embodiment). The second F indicia is laterally displaced from the F control knob 120 and is defined by a multiple waveforms 120a and an adjacent horizontal line with left and right arrows. The left arrow indicating application of the greater frequency of pulsatile gas with the complementary rotation of the F control knob, compared with the right arrow indicating application of the lesser frequency of pulsatile gas with the complementary counter-rotation of the F control knob.

The multiple waves in graphic and lateral double-headed arrow line 122a are in direct contrast to the single wave plus vertical double-headed arrow in control graphic 118a. The multiple wave graphic shows the untrained user that more gas pulses are delivered when the user follows the left-side arrow control graphic 122a. This control graphic is further confirmed by the wider span of the bent conical indicia 122 control graphic which shows that counterclockwise movement of knob 120 increases the Freq of the gas pulses.

The multiple wave indicia 122a shows waves of equal amplitude (in contrast to the single wave indicia 118a for AMP control) and the right-side arrowhead of the lateral double-headed arrow graphic 122a immediately above the multiple pulse wave indicia graphically shows the untrained user that clockwise action of control knob 120 lowers the frequency (and this "lowering" control graphic matches the smaller arcuate span region of the bent conical indicia 122).

The importance of these control graphics is three-fold. First, the single pulse and vertical double-headed arrow line graphic 118a distinguishes an amplitude AMP control from the Freq or F control graphic which shows multiple waves and a lateral left-to-right double-headed arrow line above the multiple wave indicia. Hence in the first instance, control graphics 122a and 118a distinguish frequency versus amplitude of the gas pulses. In the second and third instances, each independent control graphic shows the untrained user what knob actuation movement increases or decreases the AMP or Freq of the pulsatile gas provided the patient as opposed to knob actuation for control over the AMP of the gas. For higher AMP, see the upper arrow at the single waveform. For higher Freq, see the left-side arrowhead above the multiple wave indicia. The reverse or lowering instruction is equally visually displayed by the control graphics. The positioning of control graphics 118, 118a, compared to knob 116 on one hand, and the positioning of graphics 122, 122a and knob 120 on the other hand further informs the untrained user of which knob controls what aspect of the control-monitor 110.

With these several control graphics or GUIs placed strategically above the control knobs (referring to the bent conical graphics, 118, 122), and laterally adjacent waveform control graphics or GUIs 118a, 122a, and instructive left-right lateral indicia and up-down vertical indicia, an untrained user can visually see how to manipulate the control knobs 120, 118 (rotate to the left or right) and what those knobs control do (based upon the single waveform and multi-waveform icons) and see the effect the gas delivery to the patient (with the displays 127, 128, 129). With this simplified graphic control display, a nominally trained person can see the sensor feedback displays 127, 128, 129 on display interface 126 and be told to follow the single waveform pulse indica amplitude (greater pulse pressure delivery to the patient) or to increase frequency of the pulsatile waves based upon the multi-waveform icon (more pulses) to the patient. The use of combinatory waveform icons and bent conical curve forms overcomes the English-language barrier in many parts of the world. The waveform icons directly adjacent the control knobs enable the use of the control-monitor by non-English speaking, nominally trained persons. Waveform iconic control graphics, used in combination with adjacent vertical and horizontal lines with double-headed arrows, and bent conical segments (showing ascending or increasing control points (and conversely descending control points)) effectively avoids the need to have English-speaking operators. The physical positioning of these iconic graphic controls with respect to the control knobs is one of the several important aspects of the present invention. Of course, reduction of these gas controls is apparent with little training (less than 1 minute). Hence the FRTC ventilator can be used by poorly trained persons caring for patients needing respiratory assistance.

Internal to control-monitor 110 is a mechanism to provide the pulsatile gas flow to gas supply tube 24. As for sensory modules, the control-monitor 110 includes an internal pressure sensor, typically converting analog gas pressure signal to a digital representation. Further modules receive the digitized pressure signals P and detect pulse amplitude (AMP mod), pulse frequency rate (Freq mod) and mean airway pressure (MAP mod). The various outputs of AMP mod, Freq mod and MAP mod are applied directly, or after signal conditioning, to AMP display 127 (bar graph), MAP numerical display 128 (such signals subject to further algorithmic processing prior to display) and frequency indicator rate display 129 (respective signals also subject to further algorithmic processing prior to display). These displays 127, 128, 129 show the conditions in the breathing head at sensory port 54.

FIG. 2A diagrammatically illustrates a cross-sectional view of breathing head 10. At proximal end 16 at the gas supply, an end cap 32 seals off the proximal end of the interior chambers or passageways of breathing head body. A diaphragm 34 is mounted at a distal location on end cap 32. Diaphragm 34 is shown in a collapsed position in FIG. 2A and is shown in an expanded position in FIG. 2B.

Figure 2B:
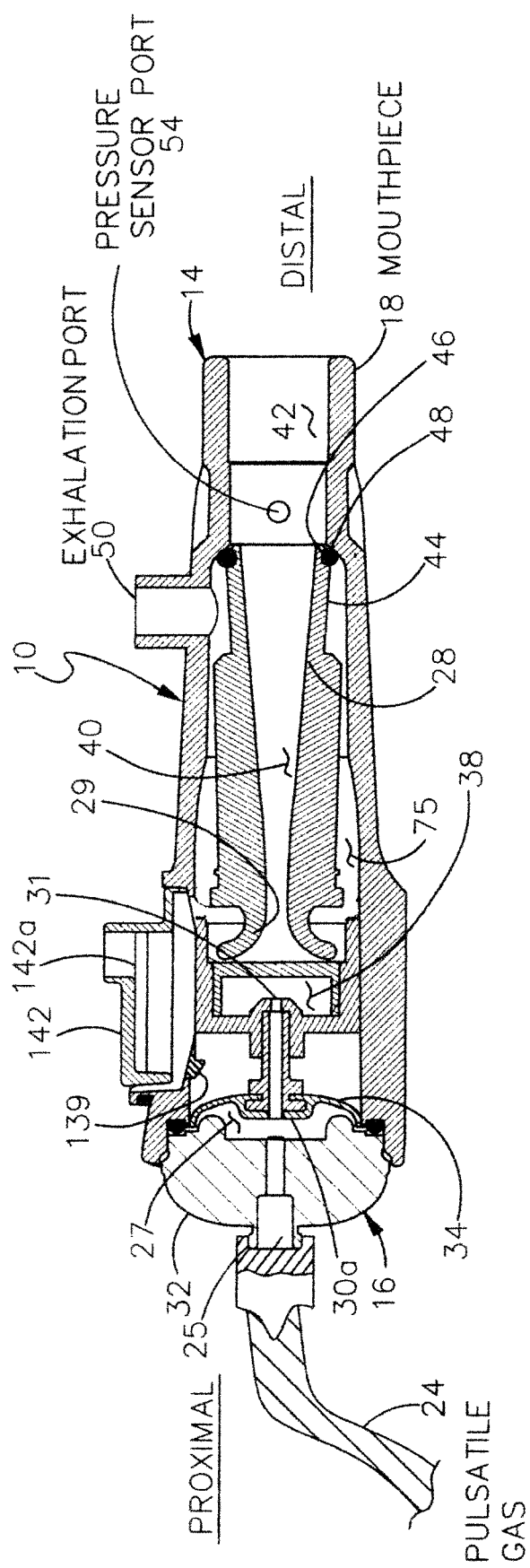
FIG. 2B diagrammatically illustrates the breathing head's injector/shuttle in its distalmost position wherein O-ring is on a valve seat.

In FIG. 2A, injector body or shuttle 44 is generally at its proximal position location. FIG. 2B shows injector/shuttle 44 generally at its distal location wherein O-ring 46 is seated against valve seat 48 formed in the interior passageway of breathing head 10. The terms "distal" and "proximal" are referenced to tube coupler portion of the breathing head, that is, "proximal" being near or closer to the tube fittings 25 and "distal" referring to items further away from the fittings (as a further example, the mouthpiece 18 of the percussive ventilation breathing head 10 is distal to tube fitting 25 in FIG. 2A).

Gas pulses are fed into proximal chamber 38 from pulsatile gas tube 24. The color-coded pulsatile gas tube 24 is connected to similarly color-coded aerosol fitting 23 at the proximal side of the breathing head 10.

Injector or shuttle body 44 defines an interior elongated flow chamber 40 having variable radial dimensions from a generally narrow proximal region 29, near proximal chamber 38, leading distally towards the distal injector/shuttle region 28, generally near O-ring 46. The proximal flow end region 29, near the venturi-like jet, is smaller than the flow region near distal region 28. Hence, distal movement of shuttle 44 injects gas pulses into the patient's airway.

Exhalation port 50 is defined on the top of the breathing head body 10. Mouthpiece 18 defines a distalmost end of flow chamber 42. A gas sensor pressure port 54 is also defined at a distal location beyond exhalation port 50 in the breathing head body 10. The gas sensor pressure body port 54 (FIG. 2B) is fluidly connected to a longitudinal feedback passage 12, FIG. 4, (the passage may be defined by a transparent body element, thereby permitting a visual indicator of excessive liquid in the chambers 40, 42), which passage extends proximally to sensory hose coupler 26*a*.

An entrainment port 142, FIG. 2B, is disposed at a generally proximal location on the breathing head body 10. Entrainment port 142 includes an entrainment gate 142*a* and the gate and port are in fluid or pneumatic connection with proximal chamber 38 at the output of the venturi-like jet.

FIG. 2B diagrammatically illustrates injector/shuttle 44 in its distalmost position wherein O-ring 46 is on valve seat 48. In this distalmost position, injector/shuttle 44 prohibits all flow through exhalation port 50. The distalmost position of shuttle 44 defines an inhalation phase. Also, pulsatile gas through end cap passage 25 has expanded the proximal chamber 27 on the proximal side of diaphragm 34, moving injector/shuttle in a distal direction while forcing the pulsatile gas flow through narrow channel 30*a* forming the input channel for venturi-like jet 31. The jet output and other pneumatic conditions in the breathing head cause the shuttle 44 to distally move. Color-coded pulsatile gas tube 24 is attached to matching color-coded fitting 25 in end cap 32 such that the pulsed gas is fed into first, the proximal diaphragm chamber 27, then through venturi input channel 30*a* and ultimately into aerosol flow channels 40 and 42. The pulsatile gas ejected from venturi channel 31 carries with it ambient gas. Entrainment gate 142*a* provides ambient gas.

Figure 3:
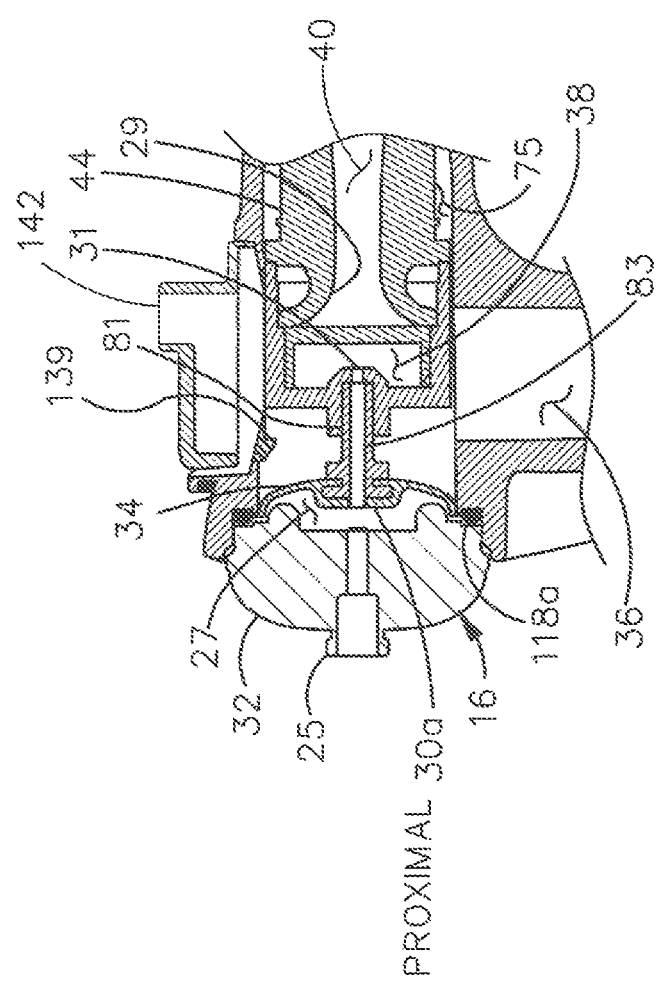
FIG. 3 diagrammatically illustrates a detailed view of the proximal portion of the FRTC ventilator breathing head and particularly the venturi-like jet formed nozzle. The shuttle is in its distal most position.

FIG. 3 diagrammatically illustrates a detailed view of the proximal portion of the percussive ventilation breathing head and particularly the venturi-like jet formed at nozzle end 31. In FIG. 3, pulsatile gas pressure has caused diaphragm 34 to expand proximal diaphragm space 27. The venturi jet sub-system includes a stem 83 which distally extends into channel passage 81 formed at the proximalmost end of the injector/shuttle 44.

Figure 5A:
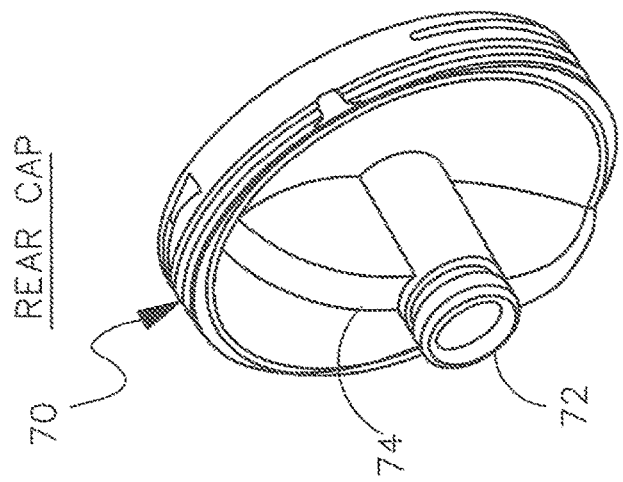
FIGS. 5A, B, C and D diagrammatically illustrate the rear cap.
Figure 5B:
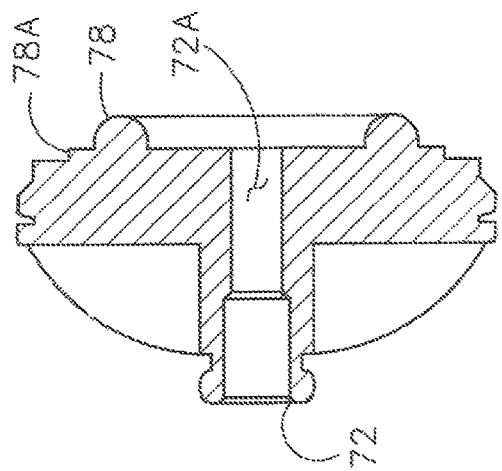
Figure 5D:
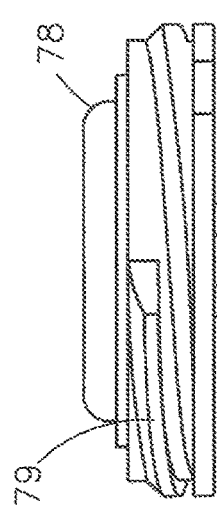
Figure 5C:
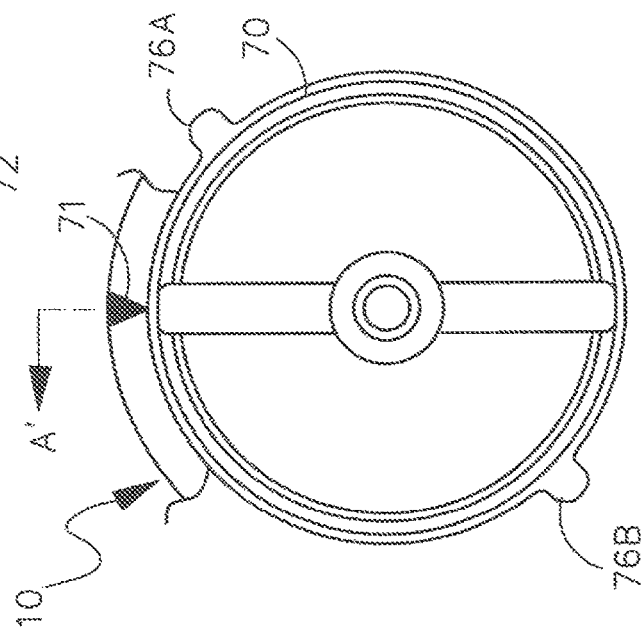

Diaphragm 34 has, at its proximal-most portion, a circumferential O-ring type seal ring 118. O-ring seal 118 is seated between a ledge in the proximal region of the breathing head body and ring seal surface 78A in FIG. 5B. Circumferential distally protruding ridge 78 in FIG. 5B captures a complementary diaphragm leg element on the diaphragm 34 as shown in FIG. 3.

In the disassembled state shown in FIG. 4, although the end cap 70 (FIG. 5A) is not shown removed from percussive ventilation breathing head body, in one construction, the venturi jet sub-system (which includes stem 83) is attached to the proximal end region of shuttle 44, and the diaphragm remains mounted the proximal end of stem 83 (that is, the diaphragm is attached to the venturi-like nozzle). When the end cap 32 is unscrewed via the female threads on the proximal end region of the breathing head body (FIG. 5A), the O-ring seal 118 of the diaphragm is opened and the diaphragm, venturi jet sub-system (which includes stem 83) remains attached to and mounted to the proximal end region of shuttle 44. This diaphragm, venturi jet and shuttle 44, as a single attached sub-system, is then removed (in addition to the spring 45, FIG. 4) from the breathing head body. The diaphragm O-ring seal 118*a* would then be the proximalmost element on the shuttle sub-system. This is a first construct of the end components.

In a second construction, with attention given to FIG. 3, the venturi-like nozzle is mounted on the distal side of the diaphragm 34. In the second construct, stem 83 is removable from channel 81 on the proximal side of the shuttle 44. The venturi-like nozzle then remains mounted onto the distal side of the diaphragm. Therefore, at disassembly, the end cap is separated from the diaphragm due the released O-ring seal 118, the diaphragm/venturi-like nozzle is separated from the shuttle 44, the spring 45 is removed from the body of the percussive ventilation breathing head, and then the shuttle 44 is removed from the breathing head body. When constructed, there is a seal between stem 83 and the distal end of channel passage 81.

In a third construct, the venturi-like nozzle is fixedly mounted to the proximal end of shuttle 44 and there is a seal between the proximal end of stem 83 and the distal end of diaphragm 34. In this third construct during disassembly, end cap 32 is unscrewed, O-ring seal 118 is opened, the seal between the proximal end of stem 83 and the distal end of diaphragm 34 is opened, and then the proximal end of the shuttle 44 includes the entirety of the venturi-like nozzle, including stem 83. The venturi-like nozzle and stem 83 is fixedly mounted to the proximal end of the shuttle 44. In the third alternative embodiment, the proximal end of stem 83 is removably seated against a distal seal at an output port of diaphragm 34.

Operationally, the percussive ventilation breathing head administers intermittent percussive ventilation to a patient's airway.

The pulsatile gas passes through a proximally disposed venturi-like passageway 38, through proximal space 38, flow passages and ports 29, 40 and 42 and into a mouthpiece 18 at a distal end 14 of the breathing head 10 and further into the airway of the patient to begin inflation of the patient's lungs during commencement of the inspiratory phase.

The pulsatile gas generally passes around and through the reciprocating injector body or shuttle 44 movably mounted in the breathing head passageway. The injector body or shuttle 44 includes outboard radial ribs 33 (see FIG. 4) permitting the pulses to pass over the injector body or shuttle from the proximal location 38 of the breathing head 10 to a distal location 42 which defines the mouthpiece 18 for the breathing head 10. In the event that a coupler 57 (see FIG. 4) is mounted on the mouthpiece 18, the patient's mouth is far removed at a distal location 14 but is fluidly connected via a tube, not shown in the drawings.

To continue with the inspiratory phase with cyclic percussion, pulses of gas are supplied to the percussive ventilation breathing head through a separate color-coded pulsatile supply line 24 at a proximal end 16 of the breathing head and these pulses of gas overwhelm the venturi orifice at the proximal end of the breathing head. These pulsatile gases, during a peak gaseous flow cycle, inflate a diaphragm space 27 in the proximal portion of the breathing head to overcome the reactive force in the diaphragm and thereby cause movement of the injector body or shuttle 44 to move in a distal direction 14 toward the mouthpiece 18 causing the distalmost portion of the injector body or shuttle 44 to form a seal with an O-ring 46 against a valve seat 48 in the distal cavity region of the breathing head. At this maximal distal end, the O-ring seals off injector body/shuttle 44 against a valve seat 48 and this seal closes off an exhalation port 50 in the breathing head body thereby delivering a pulse of aerosol laden gas into the patient's lungs. This aerosol is optionally provided. As a result, the pulsatile gases are supplied through the diaphragm-defined space 27 to a venturi input orifice and through the venturi-like passageway 38 and into the patient's airway via the mouth 18 of the breathing head 10.

During the supply of these pulsatile gases, the shuttle or injector body repeatedly reciprocates back and forth between closed and open positions with the valve seat at the proximal end of the breathing head based essentially on the pulsed gas cycles. See Freq controls and GUIs at 120, 122, 122*a*. A spring 45 (FIG. 4) biases the injector/shuttle 44 to a proximal, contracted diaphragm position (FIG. 2A). The percussive ventilation breathing head 10, at one or more interior locations, may define one or more shuttle stops which limit the proximal-most shuttle position. For example, see stop 139 in FIG. 2B. Other stops may be employed. Other biasing systems may be used such as a resilient band or bands, a plurality of springs, springs biasing in both distal and proximal directions, or a pneumatic push-back system porting pressurized gas to the biasing mechanism such as a piston or a secondary diaphragm acting on the shuttle. The application of expanding gas pressure in the pulsatile gas flow expands the diaphragm-defined space 27 and the pulsatile gas is fed through the venturi-like jet to the flow passages 40, 42 while forcing the injector/shuttle 44 against the valve seat 48. The peak portions of the gaseous cycles force the injector/shuttle against the distal breathing head against seal 48 multiple times and during the lower pressure gas valleys, the proximal diaphragm-defined space behind the injector/shuttle has less pressure and the injector/shuttle 44 moves in the proximal direction thereby opening O-ring/valve at the distal end of the injector/shuttle and further opening the exhalation port 50. The spring 45 assists in the return of the injector/shuttle 44. Hence, the reciprocating shuttle opens and closes the exhalation port 50.

Although the gases are released through the exhalation port with each opening of the exhalation port, there is only a partial release of the gas from each cyclic pulse until a maximum inflated pressure achieved given the patient's capacity. The maximum inflated pressure is determined by the patient's breathing cycle and lung capacity. This can be measured by pressure sensor port 54, color-coded sensor line 26 and pressure monitors in gas supply/controller/monitor 110.

A diaphragm 34 is mounted at a proximal position in the breathing head 10 and is also connected to an end cap 32 at the proximal end 16 of the injector/shuttle 44. The injector/shuttle 44 is moved to its distalmost position in the breathing head body 10, by the expanse 27 of diaphragm 34 at the proximal end 16 of the breathing head and by the pulsatile gas pressure at port end 29 of shuttle 44. The shuttle movement reduces spaces 40, 42 optionally filled with aerosol. Thereafter during lower pressure gas cycles, the diaphragm 34 biases, collapses or pulls back the injector/shuttle away from its distalmost position/valve sealed position and towards the open valve position of FIG. 2A.

As soon as the high-pressure pulse cycle of gas is terminated from the pulsating gas supply line (at the low-pressure cycle), the diaphragm 34 with its retracting memory returns the injector or shuttle 44 to its proximal-most position to again open the expiratory port 50 to provide partial release of expiratory gases. Therefore, there is a rapid opening and closing of the expiratory port 50 in accordance with the frequency of the pulsatile gases at certain cyclical rates.

When the patient desires to exhale, the patient exhales against the incoming pulsatile gases and creates a pressure against the proximal diaphragm 34 to overwhelm the forces applied to the diaphragm 34 and move the injector body or shuttle away from the distal valve seat 48 thereby opening the valve at the proximal location (FIG. 2A) of the breathing had body.

During the inhalation phase, at any time that the demand of the patient exceeds gas pressure supply, ambient air is introduced into flow chambers 40, 42 via port 142 and the permitted in-going ambient gas pressure defined by entrainment gate 142*a*. This entrainment of ambient air greatly enhances uninterrupted therapeutic delivery during the inspiratory phase at or near the metered start of the percussive injection of pulsatile gases into the airway the patient.

When the physiological airway pressure increases to or beyond the selected fluid clutching pressure (which may be characterized as a venturi stalling pressure) within the injector body or shuttle, the ambient entrainment gate 142a is activated. As explained in U.S. patent application Ser. No. 16/391,481, filed Apr. 23, 2019, incorporated herein by reference thereto, the entrainment gate permits ambient airflow into the shuttle chamber at one pressure, and permits outgoing gas through port gate 142a and port 142 at a different pressure. This in-going flow maintains a potential directional ambient air flow in and around the injector body or shuttle 44 to an ambient and the exhalation port 50 at all times.

The components of the present invention include breathing head assembly 10, having a distal end 14 and a proximal end 16 (which is farther away from patient mouthpiece assembly 18), a venturi-like chamber 38, and a reciprocating injector body or shuttle 44. The reciprocating injector body or shuttle 44 provides step-wise pulsatile aerosol to the patient. The breathing head assembly 10 includes a hollow body cavity 11 (FIG. 2A) within which the shuttle 44 opens and closes the aerosol flow by coacting against a step valve seat 48 in flow passage 42. The breathing head further includes a pressure sensor port 54 (FIG. 2B), which is an input to a longitudinal channel 12 leading to a color-coded nozzle 26*a* (FIG. 4), connectable to a similarly color-coded sensory tube 26, coupled at the other end to the similarly color-coded sensory coupler on the control-monitor which monitors pressure in the central flow passage 40, 42. Port 54 is disposed in an upper region of channel 12. At the proximal end 16, the central flow passage 40 has a diaphragm 34 with a retracting memory which, in cooperation with the pulsatile gas flow fed into the flow passage 40 generates or assists the pulsatile and shuttle action of the shuttle 44 in the hollow body breathing head. An entrainment port 142 is used to admit ambient air into flow passage 40. The ambient entrainment gate 142 is shown in FIG. 2B. The breathing head also has an exhalation port 50. When an O-ring 46 (see distal end of the shuttle 44) is seated on valve seat 48, flow at the exhalation port 50 is blocked (OFF).

The resulting breathing head can be made sterile with its biocompatible gas pathway and airway. Further, it is easier to clean open the hollow body with the removable rear cap 32 and withdraw the spring 45 and the shuttle 44. Spring 45 is disposed in percussive ventilation breathing head space 75. In FIGS. 2A and 2B, spring 45 is not shown.

FIG. 4 diagrammatically illustrates breathing head 10 partly disassembled. Valve port stem 26A is adapted to be coupled to a complementary valve fitting at the end of pressure monitoring line 26 shown in FIG. 1A. A transparent passageway 20 is in fluid communication with pressure monitor tube 26 and further with pressure sensing port 54 shown in FIG. 2A. In FIG. 2A, diaphragm 34 is made of medical grade silicone. In the disassembled cleaning mode (FIG. 4) the end cap is unscrewed and removed from breathing head body, the shuttle 44 and shuttle-connected pieces are withdrawn, the spring or biasing elements withdrawn and the body and other components are cleaned. If proximal shuttle stop 139 is present (see FIG. 2B), the proximal end region of the shuttle 44 may have a peripheral groove extending longitudinally, which, when the shuttle slightly rotated, and then longitudinally withdrawn from body 10, the peripheral groove forms a passage for stop 44. Alternatively, stop 139 could be omitted and proximal movement of shuttle 44 is limited by diaphragm 34 and end cap 32.

Spring 45 biases the injector body or shuttle 44 in a proximal position away from valve seat 48 (see FIG. 2A). The injector body 44 and spring 45 can be withdrawn from the interior passageway of the breathing head body for cleaning. In one embodiment, the spring is disposed at the distal ends of ribs 33 (FIG. 4) and the on the valve seat 48. However, the proximal and distal spring stops can be located in other regions of breathing head space 75. An interior exhalation portal is in fluid communication with exhalation port 50 shown in FIGS. 1A and 2A.

Supplemental mouthpiece 54 has a proximal end 57 which fits within the mouthpiece 18 defined at distal end 14 of breathing head 10. The supplemental mouthpiece 54 is inserted as shown by arrow 59 into the mouthpiece 18 of breathing head 10 in FIG. 4. Supplemental mouthpiece 54 includes a distal end portion 55 which has an oval orifice. Accordingly, supplemental mouthpiece 54 can be removed to facilitate the cleaning of breathing head 10.

FIGS. 5A, 5B, 5C and 5D diagrammatically illustrate the details of rear cap 70. Rear cap 70 includes a user actuation rib 74. In FIG. 2A, end cap 32 is shown. At the centerline of user actuation rib 74 is a male valve port stem 72 (aerosol valve fitting 25 in FIG. 2A) which pneumatically couples the rear cap passageway 72A to pulsatile pressure supply tube 24 shown in FIG. 1. Male aerosol valve port stem 72 cooperates with a complementary female aerosol valve fitting at the terminal end of pulsatile pressure supply tube or line 24.

End cap passageway 72A permits the introduction of pulsatile pressurized air into venturi-like chamber 38 shown in FIG. 2A. Circumferential rib 78 at the distal end of cap 32 retains diaphragm 34 shown in FIG. 2A. Mechanical stop nubs 76A, 76B limit the rotation of rear cap 32 due to complementary stop element 77 shown at the proximal end of breathing head body 10 in FIG. 2A. The sides of rear cap 32 define a threaded surface 79.

The rear cap 32 has a screw surface 79 with stop limiters 76A, 76B, marked to match with stop element 77 (see FIG. 2A). These stop limiters 76A, B provide a visual lock indicator to the user or patient. Visual lock indicator lines 71 on the proximal end of breathing head body are aligned with the user actuatable rib 74. Also, complementary visual markers 71, such as arrows, lines or matching unique visual elements are used which show when the rear member cap 32 is in the full locked position. Other visual indicia may be used. The mechanical stops 76A, 76B on the outside of the screw elements 79 also provide tactile feedback to the user to assure that the end cap 32 is in the fully engaged, locked position.

The percussive ventilation breathing head and end cap include one or more locking mode elements. One locking mode element includes a mechanical stop sub-system formed by cooperating stop elements on said end cap and said percussive ventilation breathing head. See FIG. 5C, stop element 76A and FIG. 2A, stop element 77. Another locking mode element is a pair of visual indicia adapted to the aligned located on the end cap 70 (FIG. 5C), with visual tab element 74 on the end cap 70 and the visual indicia “arrow” 71 on the percussive ventilation breathing head body 10.

A third locking mode element is an audible click lock indicator formed by a pair of complementary detents formed on said end cap and said percussive ventilation breathing head. The audible click lock indicator is an audible and tactile response. As a result of the flexion of a tab over small detent ridge, a tactile indicator is generated as well as an audible indicator.

In the same manner, rear cap 70 may define a small tab in the thread system which passes over a small protruding detent on the percussive ventilation breathing head body 10, generating both an audible click-to-lock indicator and a tactile click-to-lock indicator. The protruding detent and the recessive or channel detent can be formed on either the body 10 of the end cap 70. The tactile click lock indicator is described above as being formed by a pair of complementary detents formed on the end cap and the percussive ventilation breathing head.

The breathing head also includes a patient measuring port with visibility window passage 12. FIG. 1A shows that a visibility window passage runs nearly the entire length of the elongated breathing head 10. FIG. 2A shows pressure sensing port 54 pneumatically and hydraulically in fluid communication with distal passage 42 of the breathing head body. Pressure sensing port 54 is at the distal entry way into visibility window passage 12.

During the breathing cycle of the patient, sometimes droplets accumulate in the interior head passageway 42 and injector/shuttle passageway 40 because of the two-way patient breathing cycle through the passageways 40, 42. Visibility window 12 permits the patient or user to determine if there is an unacceptable accumulation of mucus or excessive liquid accumulation within the interior passages 40, 42 of the breathing head 10. Further, if there is a drop or a loss of pressure on pressure sensing line 26, the patient or healthcare worker can view the window passage 12 to determine the status of the pressure sensing line and reason for the drop in pressure. Therefore, view passage 12 provides a visual feedback to the patient and care giver.

View passage 12 can be cleaned by inserting a medical grade 3 mm pipe cleaner into the channel once the pressure line 26 (FIG. 1A) is uncoupled from the breathing head.

Figure 6:
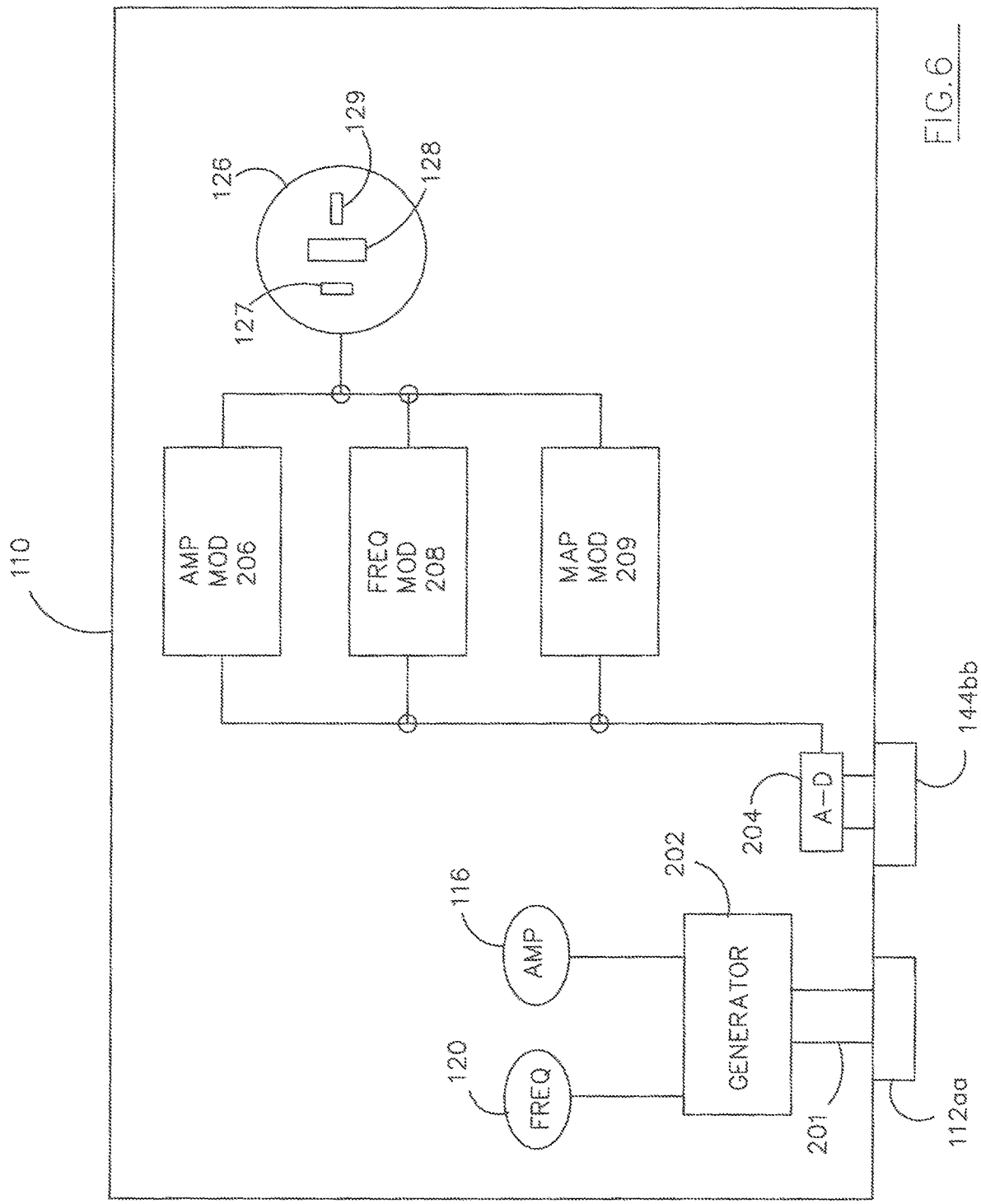
FIG. 6 diagrammatically illustrates various components in the control-monitor casing.

FIG. 6 diagrammatically illustrates various components in the control-monitor casing. Control-monitor 110 is used in combination with a percussive ventilation breathing head 10. Head 10 is adapted to be supplied with a flow of pulsatile gas from the control-monitor. The breathing head has an elongated breathing head body (FIG. 1A) adapted to be supplied with the pulsatile gas flow via a supply line 24 at a gas supply port fitting 25 at a proximal end of the breathing head body. The breathing head body defines an interior passageway 38, 42, and a reciprocating injector shuttle 44 movable in the interior passageway 38, 42. The shuttle 44 is adapted to move distally due to the pulsatile gas against a proximal bias in the interior passageway. The shuttle 44 defines an internal flow passage 40 therein from a proximal shuttle input port to a distal shuttle output port. A sensory port 54 (permitting the sensing of pressure in distal chamber passage 42) is disposed at a distal region of the interior passageway 38, 42. The sensory port 54 is fluidly coupled via a feedback passage 14 (FIG. 4) to a proximal sensory tube fitting 11 (FIG. 1A).

The control-monitor 110, see FIG. 6, includes a control-monitor casing (FIG. 1A), a sensory tube receptor fitting 114aa (FIG. 6), and a gas supply tube receptor fitting 112as on the casing. A pressure sensory tube 26 leads from the sensory tube fitting 11 to the sensory tube receptor 114bb. A gas supply tube 24 leads from the gas supply tube receptor 112aa to the gas supply port fitting 25 on the breathing head.

The casing 110 contains therein a pulsatile gas generator module 202, a pulse amplitude module 206, a pulse frequency module 208, and a mean airway pressure (MAP) module 209, respectively sensing pulsatile gas amplitudes, frequency and MAP in the sensory tube 26. Optionally, the system includes an analog to digital converter to convert the analog pressure in line 24 to digital signals customarily applied to the amplitude module 206, frequency module 208 and MAP module 209. The a-to-d converter and modules 206, 208, 209 may be a single sensory and signal processing unit. These modules 206, 208, 209 are electronically coupled to respective displays 127, 128, 129 on the display 126 of casing 110, to display sensed amplitude, frequency and MAP signals. The operational aspects of modules 206, 208, 209 are known to persons in the art.

The pulsatile gas amplitude control knob 116 and the pulsatile frequency control knob 120 effects and controls generator 202 which generates pulsatile gas supplied to the gas supply tube 24 and ultimately applied to the interior passageway 38, 42 of the breathing head 10.

The claims appended hereto are meant to cover modifications and changes within the scope and spirit of the present invention.

What is claimed is:

1. A control-monitor, in combination with a percussive ventilation breathing head adapted to be supplied with a flow of pulsatile gas from the control-monitor, the breathing head having an elongated breathing head body with a proximal end and a distal end and adapted to be supplied, at its proximal end via a gas supply tube, with the pulsatile gas flow from a pulsatile gas supply controlled by the control-monitor, the breathing head body defining an interior passageway therein, a reciprocating injector shuttle movable in the interior passageway, the shuttle adapted to move distally due to the pulsatile gas flow against a proximal bias in the interior passageway and eject gas through a shuttle internal flow passage and through the breathing head's interior passageway, the breathing head having a sensory port at a distal region of its interior passageway which sensory port is fluidly coupled to a pressure sensory tube leading to the control-monitor, the control-monitor comprising:

a control-monitor casing adapted to be fluidly connected to the gas supply tube and the sensory tube;

a pulsatile gas generator module in the casing adapted to supply pulsatile gas via the gas supply tube to the breathing head;

a pulse amplitude module, a pulse frequency module and a mean airway pressure (MAP) module sensing pulsatile gas amplitudes, frequency and MAP in the sensory tube wherein respective outputs from the amplitude, frequency and MAP modules are applied to corresponding amplitude, frequency and MAP displays on the casing;

a pulsatile gas amplitude control knob and a pulsatile frequency control knob to control the pulsatile gas generator module and effect the pulsatile gas flow supplied to the breathing head;

first and second amplitude (AMP) control indicia adjacent the amplitude control knob;

the first AMP indicia defined by a bent conical AMP indicia with a wide conical AMP span, indicating application of a greater gas amplitude with a complementary rotation of the amplitude control knob, compared with a narrow conical AMP span, indicating application of a lesser gas amplitude with a complementary counter-rotation of the amplitude control knob;

the second AMP indicia defined by a single waveform and an adjacent vertical line with up and down arrows, the up arrow indicating application of the greater gas amplitude with the complementary rotation of the amplitude control knob, compared with the down arrow indicating application of the lesser gas amplitude with the complementary counter-rotation of the amplitude control knob;

first and second frequency (F) control indicia adjacent to the frequency knob;

the first F indicia defined by a bent conical F indicia with a wide conical F span, indicating application of a greater frequency of pulsatile gas with a complementary rotation of the frequency control knob, compared with a narrow conical F span, indicating application of a lesser frequency of pulsatile gas with a complementary counter-rotation of the frequency control knob; and the second F indicia defined by multiple waveforms and an adjacent horizontal line with left and right arrows indicating application of either greater frequency of pulsatile gas with the complementary rotation of the frequency control knob or indicating application of the lesser frequency of pulsatile gas with the complementary counter-rotation of the frequency control knob.

2. The control-monitor, in combination with a percussive ventilation breathing head, as claimed in claim 1 wherein:

the first AMP indicia is disposed immediately adjacent and above the amplitude control knob and the second AMP indicia is disposed immediately adjacent and laterally displaced from the amplitude control knob, and the single waveform is a vertical single waveform;

the first F indicia is disposed immediately adjacent and above the frequency control knob and the second F indicia is disposed immediately adjacent and laterally displaced from the frequency control knob.

3. The control-monitor, in combination with a percussive ventilation breathing head, as claimed in claim 1 wherein:

the pulsatile gas amplitude control knob is adapted to increase gas amplitude with an amplitude counterclockwise turn and the pulsatile frequency control knob is adapted to increase frequency of the pulsatile gas with a frequency counterclockwise turn;

the first AMP indicia is disposed immediately adjacent and above the amplitude control knob and the second AMP indicia is disposed immediately adjacent and to the right of the amplitude control knob, and the single waveform is a vertical single waveform;

the first F indicia is disposed immediately adjacent and above the frequency control knob and the second F indicia is disposed immediately adjacent and to the right of the frequency control knob.

4. The control-monitor, in combination with a percussive ventilation breathing head, as claimed in claim 3 wherein:

the wide conical AMP span is on the left side above the amplitude control knob; and the wide conical F span is on the left side above the frequency control knob.

5. The control-monitor, in combination with a percussive ventilation breathing head, as claimed in claim 1 wherein:

the pulsatile gas amplitude control knob is adapted to increase gas amplitude with an amplitude clockwise turn and the pulsatile frequency control knob is adapted to increase frequency of the pulsatile gas with a frequency clockwise turn;

the first AMP indicia is disposed immediately adjacent and above the amplitude control knob and the second AMP indicia is disposed immediately adjacent and to the left of the amplitude control knob, and the single waveform is a vertical single waveform;

the first F indicia is disposed immediately adjacent and above the frequency control knob and the second F indicia is disposed immediately adjacent and to the left of the frequency control knob.

6. The control-monitor, in combination with a percussive ventilation breathing head, as claimed in claim 5 wherein:

the wide conical AMP span is on the right side above the amplitude control knob; and the wide conical F span is on the right side above the frequency control knob.

7. A control-monitor, in combination with a percussive ventilation breathing head adapted to be supplied with a flow of pulsatile gas from a gas supply tube from the control-monitor, the breathing head having an elongated breathing head body with an interior passageway therein, a reciprocating injector shuttle movable in the interior passageway caused to distally move due to the supplied pulsatile gas against a proximal bias in the interior passageway and eject gas through a shuttle internal flow passage and through the breathing head's interior passageway, the breathing head having a sensory port in its interior passageway which sensory port is fluidly coupled to a sensory tube leading to the control-monitor, the control-monitor comprising:

a control-monitor casing adapted to be fluidly connected to the gas supply tube and adapted to supply controlled pulsatile gas to the breathing head, the control-monitor casing also adapted to be fluidly connected to the sensory tube and adapted to sense pressure in the breathing head;

a pulsatile gas generator module in the casing adapted to control the supply of pulsatile gas to the breathing head;

a pulse amplitude module, a pulse frequency module and a mean airway pressure (MAP) module sensing pulsatile gas amplitudes, frequency and MAP in the breathing head wherein respective outputs from the amplitude, frequency and MAP modules are applied to corresponding amplitude, frequency and MAP displays on the casing;

a pulsatile gas amplitude control knob and a pulsatile frequency control knob to control the pulsatile gas generator module and effect the pulsatile gas flow supplied to the breathing head;

first and second amplitude (AMP) control indicia adjacent the amplitude control knob;

the first AMP indicia defined by a bent conical AMP indicia with a wide conical AMP span, indicating application of a greater gas amplitude with a complementary rotation of the amplitude control knob, the bent conical AMP indicia further having a narrow conical AMP span, indicating application of a lesser gas amplitude with a complementary counter-rotation of the amplitude control knob;

the second AMP indicia further including a single waveform and an adjacent vertical line with up and down arrows, the up and down arrows indicating, either (a) for counterclockwise ascending AMP knob control, the second AMP indicia on the right of the amplitude control knob and the up arrow indicating application of the greater gas amplitude with the complementary rotation of the amplitude control knob and the down arrow indicating application of the lesser gas amplitude with the complementary counter-rotation of the amplitude control knob or (b) for clockwise ascending AMP knob control, the second AMP indicia on the left of the amplitude control knob, and the up arrow indicating application of the greater gas amplitude with the complementary rotation of the amplitude control knob and the down arrow indicating application of the lesser gas amplitude with the complementary counter-rotation of the amplitude control knob;

first and second frequency (F) control indicia adjacent to the frequency knob;

the first F indicia defined by a bent conical F indicia with a wide conical F span, indicating application of a greater frequency of pulsatile gas with a complementary rotation of the frequency control knob, the bent conical F indicia also having narrow conical F span, indicating application of a lesser frequency of pulsatile gas with a complementary counter-rotation of the frequency control knob; and the second F indicia further including multiple waveforms and an adjacent horizontal line above the multiple waveforms with left and right arrows, the left and right arrows indicating, either (a) for counterclockwise ascending F knob control, the second F indicia on the right of the frequency control knob and the left arrow indicating application of the greater frequency of pulsatile gas with the complementary rotation of the frequency control knob and the right arrow indicating application of the lesser frequency of pulsatile gas with the complementary counter-rotation of the frequency control knob or (b) for clockwise ascending F knob control, the second F indicia on the left of the frequency control knob, and the right arrow indicating application of the greater frequency of pulsatile gas with the complementary rotation of the frequency control knob and the left arrow indicating application of the lesser frequency of pulsatile gas with the complementary counter-rotation of the frequency control knob.

\* \* \* \* \*